United States Patent [19]

Conrow et al.

[11] 4,118,418

[45] Oct. 3, 1978

[54] 5-PHENENYLTRIS (UREYLENE) TRIISOPHTHALIC ACID SALTS

[75] Inventors: Ransom Brown Conrow, Pearl River; Seymour Bernstein, New City, both of N.Y.

[73] Assignee: American Cyanamid Company, Stamford, Conn.

[21] Appl. No.: 811,099

[22] Filed: Jun. 29, 1977

[51] Int. Cl.$^2$ .................... C07C 63/32; C07C 69/76
[52] U.S. Cl. .................... 562/439; 424/319; 424/316; 424/263; 560/44; 424/278; 260/501.1
[58] Field of Search .................... 260/518 R; 560/44

[56] References Cited

U.S. PATENT DOCUMENTS 3,839,412   10/1974   Duffy .................... 260/518 R

OTHER PUBLICATIONS

Raether et al., Chem. Abst., vol. 82, pp. 595, #139800x (1975).
Kuehle et al., Chem. Abst., vol. 84, pp. 476, #58989e (1976).
Morrison et al., "Organic Chemistry," pp. 926–927 (1964).
Hichinbottom, "Reactions of Organic Compounds," pp. 355–357 (1957).

*Primary Examiner*—James O. Thomas, Jr.
*Assistant Examiner*—James H. Reamer
*Attorney, Agent, or Firm*—Claude J. Caroli

[57] ABSTRACT s-Phenenyltris(ureylene)triisophthalic acid salts useful as complement inhibitors.

2 Claims, No Drawings

5-PHENENYLTRIS (UREYLENE) TRIISOPHTHALIC ACID SALTS

DESCRIPTION OF THE INVENTION

This invention is concerned with compounds of the formula:

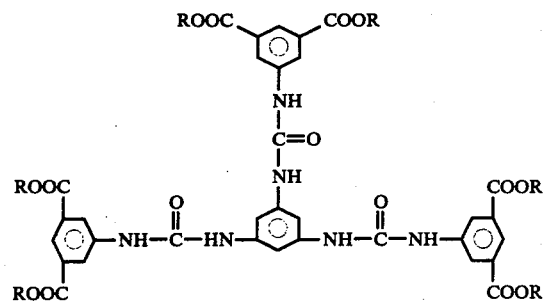

wherein R is selected from the group consisting of alkali metal; and the pharmaceutically acceptable salts thereof.

The compounds of the present invention may be prepared by reacting 5-isocyanato-di(2-methoxyethyl-)isophthalate in acetonitrile with 1,3,5-benzenetriamine. The product is isolated as the hexakis methoxyethyl ester. This ester may be converted to the hexasodium salt by treatment with sodium hydroxide.

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions," Prentice-Hall, Englewood Cliffs, N.J. (1976).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,-3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972). It has also been reported that the drug, pentosan-poly-sulfoester, has an anticomplementary activity on human serum both in vitro and in vivo, as judged by the reduction in total hemolytic complement activity; Pathologie Biologie, 25, 33–36 (1977).

SPECIFIC DISCLOSURE

EXAMPLE 1

5,5′,5″-(s-Phenenyltriureylene)triisophthalic acid hexakis (2-methoxyethyl)ester A mixture of 500 g of 5-nitroisophthalic acid, 3500 g of thionyl chloride and 6.0 ml of dimethylformamide is heated gradually until the evolution of gases subsides. Heating is continued for approximately 2 hours with stirring until solution is achieved, then reflux is continued for an additional 30 minutes. The resulting clear solution is allowed to stand, then is evaporated to an oil in vacuo. The oil solidifies and is recrystallized twice from carbon tetrachloride to give 501 g of 5-nitroisophthaloyl chloride.

A mixture of 100 g of the product above and 100 g of 2-methoxyethanol (dried over molecular sieves) in 400 ml of acetonitrile (dried over molecular sieves) is heated on a steam bath until boiling. Heating is continued for 15 minutes, then the mixture is cooled to room temperature and poured into 2 liters of cold tap water with vigorous stirring. The product is filtered off and air dried on the filter to give 129 g of material (A). Additional product (B) (5.7 g) is recovered from the filtrate by extraction with benzene. The Products (A) and (B) are dissolved in 580 ml of hot ethyl alcohol. The solution is neutralized with 5.0 ml of 5N sodium hydroxide, then diluted with 450 ml of water. The solution is allowed to crystallize at room temperature, then overnight in a chill room to give colorless needles. This material is recrystallized from 450 ml of ethanol plus 350 ml of water to give 92.1 g of 5-nitro-isophthalic acid bis(2-methoxyethyl)ester.

A total of 86.0 g of the preceding product is hydrogenated on a Parr shaker in 300 ml of ethyl acetate using 2.0 of 10% palladium on carbon catalyst. The mixture is filtered and evaporated to dryness to give off-white crystals. The crystals are dissolved in 350 ml of hot benzene and diluted with 140 ml of hexane. The solution is allowed to crystallize overnight at room temperature to yield 72.0 g of 5-amino-isophthalic acid bis(2-methoxyethyl)ester.

A solution of 3.0 g of the product above in 10 ml of methylene dichloride is added dropwise with adequate stirring to a solution of 7.4 g of phosgene in 30 ml of benzene plus 2.0 ml of pyridine, over a 15 minute period. The solution is stirred for 5 minutes then is evacuated by water pump to remove excess phosgene. The solution is washed twice with water, twice with 1N hydrochloric acid and once each with water, saturated sodium bicarbonate and water. The solution is dried over anhydrous sodium sulfate and evaporated to give 3.1 g of 5-isocyanato-di(2-methoxyethyl)isophthalate as a colorless oil.

A mixture of 1.0 g of 3,5-dinitroaniline, 0.5 g of 10% palladium on carbon catalyst and 100 ml of ethyl acetate is hydrogenated in a Parr shaker, filtered and evaporated to give 670 mg of 1,3,5-benzenetriamine.

To a stirred solution of 3.1 g of 5-isocyanato-di-(2-methoxyethyl)isophthalate (freshly prepared above) in 20 ml of acetonitrile (dried over molecular sieves) is added, in one portion, a solution of 370 mg of 1,3,5-benzenetriamine (freshly prepared) in 10 ml of dried acetonitrile. A precipitate is formed which is solubilized by the addition of 10 ml of dimethylformamide and warming. The solution is cooled and the precipitate reappears. Thirty ml of acetonitrile is added and the mixture is filtered. The precipitate is washed with diethyl ether and is dried overnight by conventional means to give 3.05 g of the product of the Example as a colorless powder, mp 223°–225° C.

EXAMPLE 2

5,5′,5″-(s-Phenenyltriureylene)triisophthalic acid hexasodium salt

To a stirred solution of 2.19 g of the product of Example 1 in 30 ml of dimethylformamide at room temperature is added 20 ml of N sodium hydroxide, followed by 10 ml of water. The mixture is stirred at room temperature for 30 minutes, warmed on a steam bath until solution is obtained and poured into 150 ml of absolute ethanol to give a fine colorless precipitate. The mixture is filtered through diatomaceous earth and the precipitate is washed on the filter with ethanol. The precipitate is dissolved off the diatomaceous earth with a total of 150 ml of hot water. The aqueous solution is concentrated in vacuo to 10–15 ml and is filtered through diatomaceous earth. The filtrate is collected and brought up to a volume of 20 ml with water. This solution is diluted with 40 ml of ethanol to yield a precipitate. The mixture is warmed on a steam bath, cooled to room temperature and filtered. The precipitate collected is washed with 15 ml of 1:2 water:ethanol, then with ethanol and ether. The material is dried to give 1.69 g of the product of the Example as a colorless powder.

EXAMPLE 3

| Preparation of Compressed Tablet | |
|---|---|
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 4

| Preparation of Compressed Tablet - Sustained Action | |
|---|---|
| Ingredient | mg/Tablet |
| Active Compound as Aluminum Lake*, Micronized | 0.5–500 (as acid equivalent) |

-continued

Preparation of Compressed Tablet - Sustained Action

| Ingredient | mg/Tablet |
| --- | --- |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 5

Preparation of Hard Shell Capsule

| Ingredient | mg/Capsule |
| --- | --- |
| Active Compound | 0.5-500 |
| Lactose, Spray Dried | qs |
| Magnesium Stearate | 1-10 |

EXAMPLE 6

Preparation of Oral Liquid (Syrup)

| Ingredient | % W/V |
| --- | --- |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

Preparation of Oral Liquid (Elixir)

| Ingredient | % W/V |
| --- | --- |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

Preparation of Oral Suspension (Syrup)

| Ingredient | % W/V |
| --- | --- |
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 9

Preparation of Injectable Solution

| Ingredient | % W/V |
| --- | --- |
| Active Compound | 0.05-5 |
| Benzyl Alcohol N.F. | 0.9 |
| Water for Injection | 100.0 |

EXAMPLE 10

Preparation of Injectable Oil

| Ingredient | % W/V |
| --- | --- |
| Active Compound | 0.05-5 |
| Benzyl Alcohol | 1.5 |
| Sesame Oil qs ad | 100.0 |

EXAMPLE 11

Preparation of Intra-Articular Product

| Ingredient | Amount |
| --- | --- |
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 12

Preparation of Injectable Depo Suspension

| Ingredient | % W/V |
| --- | --- |
| Active Compound | 0.05-5 (active equivalent) |
| Polysorbate 80 USP | 0.2 |
| Polyethylene Glycol 4000 USP | 3.0 |
| Sodium Chlorine USP | 0.8 |
| Benzyl Alcohol N.F. | 0.9 |
| HCl tp pH 6-8 | qs |
| Water for injection qs ad | 100.0 |

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every 6 hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor) — This test measures the ability of activated human C1 to destroy fluid phase human C2 in the presence of C4 and appropriate dilutions of the test compound. An active inhibitor protects C2 from C1 and C4; (ii) Test, Code O35 (C3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in vitro and in vivo, complement inhibiting activity in warm-blooded animals.

Some of the compounds of the present invention have been found to possess anti-coagulant activity as well as complement inhibiting activity. The in vitro anti-coagulant activity (AC) of the compounds of this invention has been demonstrated by the following test: Citrated sheep plasma (CSP) is added to various dilutions of test compound in a Microtiter ® plate, the CSP sample mixtures are then recalcified with an isotonic sheep red blood cell (RBC) suspension. The sheep RBC's, kept in suspension throughout the clotting incubation time, become enmeshed in the fibrin matrix if a clot forms. Upon centrifugation of the plate, untrapped RBC's form buttons, the sizes of which correspond to the degree of clot inhibition; this providing a measure of anti-coagulant activity (AC). Sodium heparin is used as a positive control and activity is reported in wells appearing in Table I.

TABLE I

| | Biological Activities | | | | | In Vivo Activity (Guinea Pig) % Inhibition | | | | | |
|---|---|---|---|---|---|---|---|---|---|---|---|
| | Cl 026* | C-Late 035* | Shunt Inhibition 036* | AC* | Cap | Intraperitoneal Time (mins.) | | | Intravenous Time (mins.) | | |
| Compound | Wells | Wells | Wells | Wells | 50* | 30 | 60 | 120 | 2 | 30 | 120 |
| 5,5',5''-(s-Phenenyltriurethylene)-triisophthalic acid hexasodium salt | +5** +6 | N N | +1** +1 | <−2** | 167 | −43 | −9 | −41 | | | |

*Code designation for tests employed as referred herein.
**Activity in wells a serial dilution assay. Higher well number indicates higher activity. The serial dilutions are tw The computation of an *Intrinsic Therapeutic Index* (*ITI*) was devised to correlate the results expressed in wells, obtained in the in vitro Code 026 (C1 inhibitor) test and the in vitro anti-coagulant (AC) test into a meaningful value which would aid in the net evaluation of the activity of the compounds of this invention.

The *ITI* of a given compound may be defined as the antilogarithm of the logarithmic (base 2) difference between the highest serial dilution in wells which is active in the Code 026 test and the highest serial dilution in wells providing activity in the anti-coagulant test. The *ITI* is thus a measure of the separation of anti-complement and anti-coagulant activities; the higher the numerical value the more therapeutically useful the separation of activities.

The *Intrinsic Therapeutic Index* of the compounds of this invention are listed in Table II.

We claim:
1. A compound of the formula:

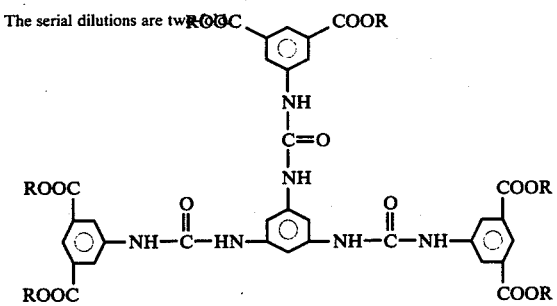

wherein R is selected from the group consisting of alkali metal; and the pharmaceutically acceptable salts thereof.

2. The compound according to claim 1, 5,5',5''-(s-phenenyltriureylene)triisophthalic acid hexasodium salt.

TABLE II

| | Intrinsic Therapeutic Index | | | |
|---|---|---|---|---|
| | In Vitro Activity | | | |
| Compound | Complement Inhibiting Activity (Wells) Code 026 | Anti-Coagulant Activity (Wells) AC | Logarithmic Difference Expressed as Wells | Intrinsic Therapeutic Index |
| 5,5'5''-(s-Phenenyltriureylene)tri-isophthalic acid hexasodium salt | +6 | −2 | +8 | 256 |